US009603797B2

(12) United States Patent
Herry et al.

(10) Patent No.: US 9,603,797 B2
(45) Date of Patent: Mar. 28, 2017

(54) ORAL AND/OR BUCCAL COMPOSITION IN THE FORM OF A THIN FILM OF A WEAKLY SOLUBLE ACTIVE INGREDIENT, METHOD OF PREPARING SAME AND USE OF SAME

(71) Applicant: ETHYPHARM, St. Cloud (FR)

(72) Inventors: Catherine Herry, Saint-Quen du Tilleul (FR); Vincent Billoet, Sotteville les Rouen (FR); Pascal Oury, Le Chesnay (FR)

(73) Assignee: ETHYPHARM, Saint-Cloud (FR)

( * ) Notice: Subject to any disclaimer, the term of this patent is extended or adjusted under 35 U.S.C. 154(b) by 0 days.

(21) Appl. No.: 14/654,766

(22) PCT Filed: Dec. 9, 2013

(86) PCT No.: PCT/FR2013/053002
§ 371 (c)(1),
(2) Date: Jun. 22, 2015

(87) PCT Pub. No.: WO2014/091134
PCT Pub. Date: Jun. 19, 2014

(65) Prior Publication Data
US 2015/0359735 A1    Dec. 17, 2015

(30) Foreign Application Priority Data
Dec. 10, 2012  (FR) ...................................... 12 61843

(51) Int. Cl.
*A61K 9/00* (2006.01)
*A61K 9/14* (2006.01)
(Continued)

(52) U.S. Cl.
CPC ................. *A61K 9/006* (2013.01); *A61J 3/00* (2013.01); *A61K 9/145* (2013.01); *A61K 9/146* (2013.01); *A61K 31/4985* (2013.01)

(58) Field of Classification Search
CPC ....... A61J 3/00; A61K 31/4985; A61K 9/006; A61K 9/145; A61K 9/146
See application file for complete search history.

(56) References Cited

U.S. PATENT DOCUMENTS

2009/0047330 A1* 2/2009 Bangalore ............ A61K 31/519
                                                              424/443
2009/0263467 A1* 10/2009 Joshi .................... A61K 9/0056
                                                              424/443
(Continued)

FOREIGN PATENT DOCUMENTS

WO    WO 2005/000265      1/2005
WO    WO 2005/013937      2/2005
(Continued)

OTHER PUBLICATIONS

International search report dated Feb. 21, 2014 in corresponding PCT Application No. PCT/FR2013/053002 filed Dec. 9, 2013.

*Primary Examiner* — Aradhana Sasan
(74) *Attorney, Agent, or Firm* — RatnerPrestia

(57) ABSTRACT

The present invention relates to an oral and/or buccal composition in the form of a thin film of a pharmaceutically active ingredient weakly soluble in water and gastro-intestinal tract fluids, comprising particles of said active ingredient dispersed in a film-forming polymer, at least 50% by weight of the total weight of the active ingredient having a particle size distribution such that at least 90% of said particles have a size below 1000 nm, preferably less than
(Continued)

800 nm, and even more preferably less than 600 nm, and to the method of preparing that composition and the use thereof.

12 Claims, 1 Drawing Sheet

(51) Int. Cl.
*A61K 31/4985* (2006.01)
*A61J 3/00* (2006.01)

(56) References Cited

U.S. PATENT DOCUMENTS

| | | | | |
|---|---|---|---|---|
| 2009/0306026 A1* | 12/2009 | Tuiten | ............... | A61K 31/4985 514/171 |
| 2011/0136815 A1* | 6/2011 | Zerbe | ................... | A61K 9/006 514/249 |
| 2012/0128740 A1* | 5/2012 | Filipcsei | ................ | A61K 9/14 424/400 |

FOREIGN PATENT DOCUMENTS

| WO | WO 2007/033239 | 3/2007 | | |
|---|---|---|---|---|
| WO | WO 2010/146407 | 12/2010 | | |
| WO | WO 2012/053006 A2 * | 4/2012 | ............... | A61K 9/70 |

* cited by examiner

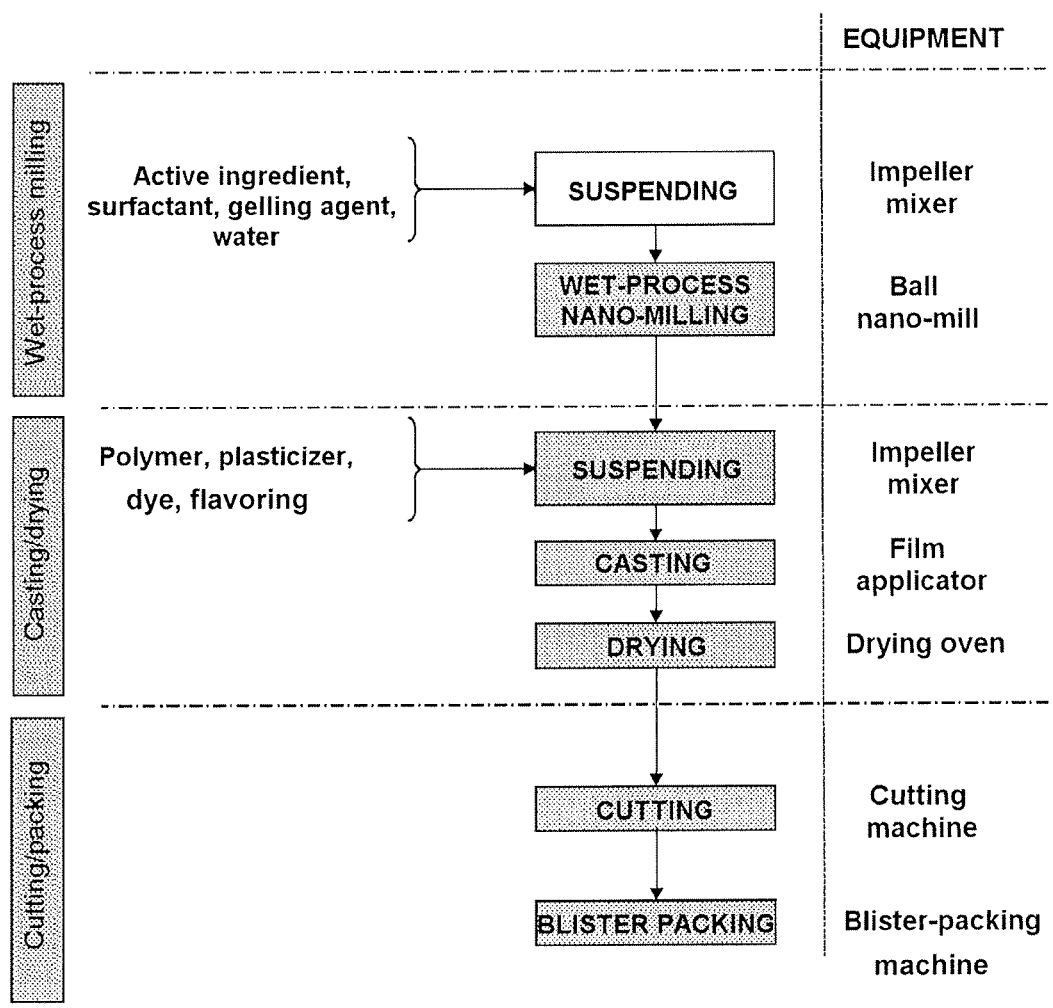

ORAL AND/OR BUCCAL COMPOSITION IN THE FORM OF A THIN FILM OF A WEAKLY SOLUBLE ACTIVE INGREDIENT, METHOD OF PREPARING SAME AND USE OF SAME

RELATED PATENT APPLICATIONS

The present application is filed pursuant to 35 U.S.C. §371 as a U.S. National Phase Application of International Patent Application No. PCT/FR2013/053002, which was filed on Dec. 9, 2013, claiming the benefit of priority to French Patent Application No. FR 1261843 filed on Dec. 10, 2012. The content of each of the aforementioned Patent Applications is incorporated herein by reference in its entirety.

The subject of the present invention is an oral and/or buccal pharmaceutical composition and also the process for producing same. Preferably, this pharmaceutical composition is provided in the form of a thin film for oral use which disintegrates in the buccal cavity and is used as a medicament.

The invention preferably comprises an oral and/or buccal pharmaceutical formulation in the form of a rapidly disintegrating film allowing the absorption of one or more active ingredients, at least one of which is not soluble or has low solubility in gastrointestinal tract fluids, at least one of them being in a nanonized particulate form. The final product described in the present invention is an orally and/or buccally disintegrating film which includes a dose of one or more therapeutic active ingredients, at least one of which has been previously nanonized.

Generally, the commercially available thin films intended for the oral and/or buccal route are produced by casting and are then cut up. An alternative method of production is a hot extrusion process.

Active ingredients which have low solubility belong to classes II and IV of the BCS (Biopharmaceutics Classification System) classification according to the FDA, class II denoting compounds which have a high permeability and a low solubility and class IV denoting compounds which have a low permeability and a low solubility. In the case of these active ingredients, obtaining a bioavailability compatible with the therapeutic effect requires formulating the active ingredient in the form of a solid solution or dispersion in a polymer (by means of an organic process or by hot extrusion).

However, it is difficult to stabilize solid solutions and dispersions, which results in recrystallization that can cause a loss of bioavailability over time. The solid solutions/dispersions obtained by means of an organic process have the drawback of containing traces of organic solvents.

Furthermore, hot extrusion processes cannot be used for thermolabile molecules and the choice of envisionable excipients is limited to hot-melt compounds.

The production of thin films which include an active ingredient in suspension is complex. This is because the non-solubilized particles tend to rapidly sediment, thereby inducing problems of uniformity of active ingredient content and also appearance defects on the final product.

An alternative to the production of solid solutions for increasing the bioavailability of active ingredients which have low solubility is to reduce the size of the particles of the active ingredient in order to increase its solubilization rate (Noyes-Whitney equation, the conventional equation developed in relation to the rate of dissolution of a substance in a solvent) and thus to maximize its in vivo absorption.

A nanosuspension of active ingredient can be stabilized with surface agents, thereby limiting the Ostwald maturation phenomenon, a phenomenon which occurs during the aging of suspensions. It involves a migration of the molecules constituting the smallest particle, to the largest particle. This phenomenon causes an increase in the average size of the dispersed-phase particles, and a narrowing of the particle size distribution of the suspension. The nanosuspension therefore guarantees a greater homogeneity of particle size over time. Furthermore, the nanosuspension can be directly used in the process for producing the film by adding the film-forming polymers, thereby facilitating the implementation thereof.

Unexpectedly, the applicant has succeeded in developing a simple and efficient process which makes it possible to reduce the size of the particles of one or more active ingredients to a nanometric level just before its/their inclusion in a thin film intended for the oral and/or buccal route.

The object of the present invention is to provide an oral and/or buccal composition in the form of a thin film which does not have the drawbacks of the prior art films. This film is uniform (active ingredient content and appearance), stable over time, in particular with regard to the size of the active ingredient particles, and avoids any use of solvents other than water for the production thereof.

In particular, an object of the invention is to provide a soluble thin film which makes it possible to avoid non-uniformity of the active ingredient within the film through the use of a nanosuspension, while at the same time increasing the bioavailability of the active ingredient.

According to the invention, the term "nanosuspension" should be understood to be a suspension, in a solvent in which the active ingredient is not soluble, preferably water, of the very finely milled active ingredient, at least 90% of the particles of which (D(90)) have a size of less than 1000 nm, preferably less than 800 nm, and even more preferentially less than 600 nm. The size of the particles is determined by laser-diffraction or light-scattering particle size.

The term "bioavailability" is intended to mean the fraction of the dose of medicament administered which reaches the general circulation.

Thus, according to a first subject, the invention relates to an oral and/or buccal composition in the form of a thin film of a pharmaceutically active ingredient which has low solubility in water and gastrointestinal tract fluids, comprising particles of said active ingredient dispersed in a film-forming polymer, at least 50% by weight of the total weight of active ingredient having a particle size distribution such that at least 90% of said particles have a size of less than 1000 nm, preferably less than 800 nm, and even more preferentially less than 600 nm.

The film-forming polymers used for the production of the compositions according to the present invention, in particular of the orodispersible films, may be of natural origin, such as pectins, starch derivatives such as pullulans or algal derivatives such as, for example, alginates. Cellulose-based derivatives may also be used, such as ethylcellulose, hydroxypropylmethylcellulose, hydroxypropylcellulose, hydroxymethylcellulose or hydroxyethylcellulose, and also microcrystalline celluloses. Biodegradable hydrophilic polymers can also be used in the compositions of the present invention, in particular polyvinyl alcohols and modified polyvinyl alcohols or else polyvinylpyrrolidones (PVPs), also known as polyvidone or povidone, polyols such as polyethylene glycols (PEGs), also known as polyoxyethylene, and modified starches.

According to the invention, the polymeric base used for the production of the film may be a single polymer or a blend of various polymers in various ratios.

The active ingredients used in the compositions described in the present invention are active ingredients with low solubility in water and gastrointestinal tract fluids. They are classified in classes II and IV of the BCS classification, without, however, being limited thereto.

Preferentially, the active ingredients used in the compositions described in the present invention can be selected from a variety of classes of known medicaments, for instance analgesics, opiate substitution products, anti-inflammatories, anti-arrythmics, antibiotics (including penicillins), anticoagulants, antidepressants, antiepileptics, antihistamines, antihypertensives, immunosuppressants, anxiolytic sedatives (hypnotics and neuroleptics), astringents, adrenergic beta-blockers, cough suppressants, lipid-regulating agents, muscle relaxants, vasodilators and phosphodiesterase inhibitors, such as xanthines, but are not limited to these therapeutic classes. The preferred active ingredients comprise those intended to be administered orally and/or buccally.

According to one embodiment of the invention, the active ingredient is entirely subjected to nano-milling. The composition in the form of a thin film therefore comprises the entirely nanonized active ingredient. In this embodiment, 90% of the particles (D(90)) have a size of less than 1000 nm, preferably less than 800 nm and even more preferentially less than 600 nm. The size of the particles is determined by laser-diffraction or light-scattering particle size.

According to another variant of the invention, only one part of the active ingredient has undergone nano-milling. The other part has only been dispersed in the nanosuspension. Preferentially, the part of nano-milled active ingredient is predominant (>50% weight/weight).

According to the invention, it may also be envisioned for the composition to comprise a mixture of several active ingredients with different solubilities; the active ingredient having the worst solubility is at least partly nano-milled, and the other active ingredient(s) is (are) dispersed in the nanosuspension.

Preferably, the active ingredients used in the composition according to the invention are pharmaceutical active ingredients which have a low solubility in water or gastrointestinal tract fluids and are included in the composition in an amount ranging from approximately 0.01% to 80%, preferably 1% to 50% (weight/weight of the composition).

According to one particular embodiment, the invention concerns an oral pharmaceutical form in the form of a unitary thin film suitable for oral administration, comprising approximately 0.1 mg to approximately 100 mg of the active ingredient per unitary thin film.

Additives or excipients may also be added to the composition according to the invention. They may include, without however being limited thereto: wetting agents such as surfactants, plasticizers of polyalcohol type; antifoams, such as silicone compounds, which promote a smooth surface of the film by promoting the elimination of air bubbles in the film; gelling agents such as gels of pectin, carrageenan, and gelatin, which helps to maintain the dispersion of the components, inclusion compounds, such as cyclodextrins.

Among the additives or excipients, lubricants, stabilizers, viscosifying agents, dyes, sweeteners, flavorings, flow accelerators, diluents, binders, pH buffers, and slip agents may also be included.

According to one particular embodiment, the pharmaceutical compositions of the present invention comprise one or more polymers and at least one active ingredient, and various excipients chosen from a wetting agent (surfactant), an antifoam agent, and mixtures thereof, and optionally a viscosifying agent, a flavoring, a sweetener and/or a dye.

The antifoam agents which can be used in the present invention are silicone derivatives. Simethicone is particularly useful as an antifoam agent. The use of an antifoam agent however is not limited to the use of simethicone, other antifoam agents can thus be used.

The viscosifying agents which can be used in the present invention are cellulose derivatives, gelatins, natural or modified gums, or other polymers which make it possible to increase the viscosity of water.

Advantageously, the viscosifying agent used in pharmaceutical compositions of the invention is a cellulose derivative. Preferably, the cellulose-based derivative is hydroxypropylmethylcellulose.

Preferably chosen is hydroxypropylmethylcellulose (HPMC) or hypromellose, the apparent viscosity of which is from 3 to 15 mPa·s and even more preferably from 3 to 6 mPa·s, for instance Pharmacoat 603® (low-viscosity HPMC), and it can be added to the film-forming mixture in an amount of approximately 0.1 percent by weight to approximately 50.0 percent by weight of the nanosuspension, more advantageously of approximately 1.0 percent by weight to approximately 20.0 percent by weight of the nanosuspension, and more advantageously of approximately 1.0 percent by weight to approximately 10.0 percent by weight of the nanosuspension.

The surfactant is chosen from surfactants which are solid or liquid at ambient temperature, for example sodium lauryl sulfate, Polysorbate 80 or Montane 20, preferably sodium lauryl sulfate.

Advantageously, the active ingredient is a phosphodiesterase inhibitor, preferably tadalafil included in an aqueous nanosuspension. This suspension also includes a cellulose-based derivative as a viscosifying agent, a surfactant as a wetting agent and an antifoam. The tadalafil is preferably in crystalline form, the size of the particles (D(50)) being less than 1000 nm, preferably less than 800 nm, and even more preferentially less than 600 nm.

According to one variant the tadalafil is in crystalline form, the size of the particles (D(90)) being less than 1000 nm, preferably less than 800 nm and even more preferentially less than 600 nm.

The composition in the form of a thin film according to the invention makes it possible to make available unit dosage forms in which the active ingredient is uniformly dispersed. These unit dosage forms are easily taken by the patient, thereby making it possible to improve treatment adherence. They disintegrate very rapidly in the mouth, in particular on the mucous membranes, and thus facilitate a rapid action of the active agent.

The present invention also relates to a process for preparing the thin film for oral and/or sublingual use. According to the general process of the invention, the active ingredient is suspended in a solvent in which it is not soluble, and then nanonized. Film-forming polymer is added to the nanosuspension obtained, and then the composition obtained is formed into thin films.

Thus, according to the process for preparing a composition according to the invention, successively:
  the active ingredient is suspended in a solvent in which it is not soluble,
  the particles of active ingredient are milled, at least one film-forming polymer is added,
the composition thus obtained is converted into thin films.

According to one particular embodiment, said process comprises the following steps:
- a/ suspending an active ingredient in a solvent in which said active ingredient is not soluble;
- b/ optionally, adding, to the dispersion, a wetting agent with optionally other excipients;
- c/ milling the mixture obtained in the previous step, in a ball mill until an average particle size of the active ingredient (D(50)) of less than 1000 nm, preferably less than 800 nm and even more preferentially less than 600 nm is obtained;
- d/ uniformly mixing the nanosuspension obtained with at least one polymer and optionally excipients;
- e/ casting the composition obtained in step d) on a substrate so as to obtain a film;
- f/ drying the film and optionally cutting it up.

The active ingredient is, firstly, suspended in a solvent in which it is insoluble. This solvent may be of any nature, organic or non-organic. Preferably, the solvent used for the present invention is water. Certain excipients may also be added to this suspension.

Preferentially, but not in a limiting manner, a wetting agent which allows good dispersion of the active ingredient is added to this suspension. This wetting agent may be of varied nature, but preferentially a surfactant is used, for example sodium lauryl sulfate or derivatives thereof. The surfactant represents between 0.1% and 5%, preferably between 0.3% and 3% by weight of the nanosuspension, the % being expressed relative to the total weight of the nanosuspension.

An antifoam agent may also be added in order to prevent significant foam formation. This agent is, for example, a silicone derivative, in particular simethicone, but may be of quite varied nature.

The antifoam used in the pharmaceutical compositions may be added in an amount of approximately 0.01% by weight to approximately 5.0% by weight of the nanosuspension, more advantageously of approximately 0.02% by weight to approximately 1.0% by weight of the nanosuspension, and more advantageously of approximately 0.05% by weight to approximately 0.5% by weight of the nanosuspension, the % being expressed relative to the total weight of the nanosuspension.

A viscosifying agent may also be added in order to facilitate the maintaining of the active ingredient particles in suspension. Any viscosity-modifying polymer may be used for this purpose.

It may be added in an amount of approximately 0.1% by weight to approximately 50.0% by weight of the nanosuspension, more advantageously of approximately 1.0% by weight to approximately 20.0% by weight of the nanosuspension, and more advantageously of approximately 2.0% by weight to approximately 10.0% by weight of the nanosuspension, the % being expressed relative to the total weight of the nanosuspension.

The suspension obtained is subsequently introduced into a wet-process ball nano-mill. This equipment allows the particles of active ingredient to be milled via a mechanical effect. Insoluble beads of defined size bang together and break the particles of active ingredient down to a minimum size. The size of the milling balls is less than 1 mm and preferentially less than 800 µm, preferably less than 600 µm.

Preferably, the suspension to be milled circulates in the nano-mill in a closed circuit such that the milling is as efficient as possible.

The milling is stopped when an average particle size of the active ingredient (D(50)) of less than 1000 nm, preferably 800 nm and more preferentially 600 nm is obtained.

Once the nanosuspension has been produced, the film-forming polymer is added and optionally the other excipients which allow the production of the thin film are added with stirring. Another active ingredient or non-nano-milled particles of the active ingredient already present in the nanosuspension may also be added. Once a uniform mixture has been obtained, the suspension is cast onto a substrate and then dried in an oven. The product is subsequently detached from its substrate and cut to the desired size, making it possible to form unitary films, i.e. the units to be taken.

Preferentially, but not in a limiting manner, the film according to the invention has a final water content of from 1% to 5% (w/w), preferably less than 4.5% (w/w), and even more preferentially less than 4% (w/w). The low final water content promotes the stability of the film over time.

The present invention also relates to the use of a composition for the production of a medicament for the administration of up to a maximum total dose of 20 mg of tadalafil per day for the treatment of sexual dysfunction in a patient in need of said treatment.

The invention is not limited to only the exemplary embodiments explicitly described above.

EXAMPLES

In the examples below, the percentages are percentages by weight/weight.

BRIEF DESCRIPTION OF THE DRAWING

The process carried out in the examples below is represented generally by the diagram in FIG. 1.

EXAMPLE 1

Preparation of a Nano-Milled Suspension of Tadalafil

An aqueous suspension comprising 500 mg of tadalafil is prepared in the following way.

HPMC 603 is suspended in water at ambient temperature in a suitable container and with stirring by means of a marine impeller. Sodium lauryl sulfate and a simethicone emulsion are then added, still with stirring. Finally, the active ingredient is added to this mixture with stirring until a visually uniform suspension is obtained.

A surfactant, sodium lauryl sulfate, is added in order to facilitate the suspending of the tadalafil.

An antifoam agent, simethicone, is added to the suspension in order to prevent any bubble formation.

A viscosifying agent, a cellulose-based derivative HPMC 603, is also introduced in order to promote the maintaining of the active ingredient in suspension and to promote the efficiency of the milling. The formula of the milling suspension is described in table 1.

TABLE 1

Final formula of the films

| | | Suspension of tadalafil | |
|---|---|---|---|
| | Constituents | Amount (g) | Centesimal composition* |
| | Tadalafil | 500.0 g | 20.0% |
| | Sodium lauryl sulfate | 50.0 g | 2.0% |
| | Simethicone | 5.0 g | 0.2% |
| | HPMC 603 | 62.5 g | 2.5% |
| | Purified water | 1882.5 g | 75.3% |
| | Total | 2500.0 g | 100.0% |

This suspension is prepared in a vessel of suitable size (stainless steel beaker of large volume) and mixed by means of an impeller mixer (an IKA marine impeller mixer) for the amount of time required to obtain a uniform suspension, the total mixing time being approximately one hour.

This suspension is then nano-milled in a wet-process ball mill until a suspension of which the particle size distribution of the dispersed phase has a maximum size of less than 1000 nm (nanometric size) is obtained.

EXAMPLE 2

Preparation of Orodispersible Tadalafil Films

The suspension obtained in example 1 is then used as a base for the production of orodispersible films.

The polymer which serves to form the film, which is pullulan, glycerol as plasticizer and a lemon flavoring are added to said suspension.

The quantitative formulation is described in table 2.

TABLE 2

Final formula of the films

| | | Amount (g) | Centesimal composition* |
|---|---|---|---|
| Nanonized suspension of tadalafil | Tadalafil | 500.0 g | 19.42% |
| | Sodium lauryl sulfate | 50.0 g | 1.94% |
| | Simethicone | 5.0 g | 0.19% |
| | HPMC 603 | 62.5 g | 2.43% |
| | Purified water | 1882.5 g | — |
| Pullulan | | 1340.0 g | 52.05% |
| Glycerol | | 536.5 g | 20.84% |
| Lemon flavoring | | 80.5 g | 3.13% |
| Purified water | | q.s. | — |
| Total dry weight* | | 2679.5 g | 100.00% |

The composition thus obtained is cast onto a substrate, and the film thus formed is dried in an oven to a level of about 5% to 10%.

EXAMPLE 3

Cutting Out the Orodispersible Tadalafil Films

The films, once dried, are then cut to the desired size using a hole punch. Conventionally, the size of the films cut out ranges from 1 to 2 mm in width for a length of 2 to 3 mm.

This process is applied to the film formed in example 2. The final centesimal formula of a unitary film of nanonized tadalafil 2 mm wide and 3 mm long is described in table 3.

TABLE 3

Unitary film of nanonized tadalafil 2 mm wide and 3 mm long

| | | Amount (g) | Centesimal composition* |
|---|---|---|---|
| Nanonized suspension of tadalafil | Tadalafil | 10.00 | 19.42% |
| | Sodium lauryl sulfate | 1.00 | 1.94% |
| | Simethicone | 0.10 | 0.19% |
| | HPMC 603 | 1.25 | 2.43% |
| Pullulan | | 26.80 | 52.05% |
| Glycerol | | 10.73 | 20.84% |
| Lemon flavoring | | 1.61 | 3.13% |
| Residual water | | q.s. | — |
| Total dry weight | | 42.87 | 100.0% |

EXAMPLE 4

Centesimal Composition of the Dry Film

The films presented in table 4 were prepared according to the same protocol as that described in examples 1, 2 and 3.

TABLE 4

Centesimal composition of the film

| Constituents | Mass per dry film (mg) | Amount of the dry film (%) |
|---|---|---|
| Tadalafil | 20.00 | 26.63 |
| Hypromellose 603 | 2.50 | 3.33 |
| Polysorbate 80 | 2.00 | 2.66 |
| Simethicone (emulsion) | 0.20 | 0.27 |
| Hydroxypropylcellulose SSL | 46.32 | 61.68 |
| Glycerol | 3.76 | 5.01 |
| Sucralose | 0.32 | 0.42 |
| Total (dry mass) | 75.10 | 100.00 |

Two types of films are derived from this composition, one film of which the active ingredient has been micronized and the second of which the active ingredient has been nanonized.

The final water content of these films was measured by the Karl Fisher method (Mettler Toledo apparatus).

The D50 and D90 particle size of these films was measured using a particle size analyzer (Mastersizer 2000) using laser diffraction to measure the size of the particles of the nanonized and micronized active ingredient.

The D50 and D90 particle size values and the final water content of these films corresponding to the composition of table 4 are presented in table 5 below.

TABLE 5

Particle sizes of the active ingredients used and final water content of the two films

| | D50 | D90 | % final water content (m/m) |
|---|---|---|---|
| Test 1 (micronized tadalafil) | 4 μm | 9 μm | 5% |
| Test 2 (nanonized tadalafil) | 0.1 μm | 0.2 μm | 4.1% |

Pharmacokinetic Data for the Two Types of Film (Test 1: Micronized Tadalafil and Test 2: Nanonized Tadalafil)

TABLE 6

Pharmacokinetic data for the two types of film (micronized and nanonized tadalafil

| Parameters | TEST-1 (micronized) | | TEST-2 (nanonized) | |
| --- | --- | --- | --- | --- |
| | Value | C.V. (coefficient of variation) | Value | C.V. (coefficient of variation) |
| $C_{max}$ | 375.15 | 28.9 | 454.94 | 23.8 |
| $T_{max}$ (hours) | 3.00 | 33.8 | 2.50 | 26.4 |
| $AUC_{0-T}$ | 7235.38 | 31.6 | 7810.18 | 32.5 |
| $AUC_{0-\infty}$ | 9444.30 | 44.2 | 10 293.85 | 46.0 |

Grouped together in table 6 above are the values of the comparative pharmacokinetic data for the two films comprising micronized and nanonized tadalafil.

The invention claimed is:

1. A process for preparing an oral and/or buccal composition in the form of a thin film of a pharmaceutically active ingredient which has low solubility in water and gastrointestinal tract fluids and which belongs to classes II and IV of the BCS classification, according to which, successively:
   the active ingredient is suspended in a solvent in which it is not soluble,
   the suspension thus obtained is milled in a wet-process ball nano-mill until 90% of the particles of the active ingredient (D(90)) have a size of less than 1000 nm,
   the nanosuspension thus obtained is uniformly mixed with at least one film-forming polymer,
   the composition thus obtained is converted into a thin film,
   said composition thus prepared having particles of said active ingredient dispersed in said film-forming polymer and having a final water content of from 1% to 5% (w/w).

2. The process as claimed in claim 1, wherein excipients are added:
   in the suspension obtained before being milled and/or
   in the nanosuspension obtained after the mixing of at least one film-forming polymer and before the composition is converted into a thin film,
   said excipients being chosen from wetting agents, plasticizers, antifoams, gelling agents, inclusion compounds, lubricants, stabilizers, dyes, sweeteners, flavorings, flow accelerators, diluents, binders, pH buffers, slip agents, and mixtures thereof.

3. The process as claimed in claim 1, wherein the polymer is chosen from the group consisting of pectins, modified starches, starch derivatives, algal derivatives, microcrystalline celluloses, cellulose-based derivatives, polyvinyl alcohols, modified polyvinyl alcohols, polyvinylpyrrolidones (PVPs), polyols, and mixtures thereof.

4. The process as claimed in claim 1, which wherein the prepared composition is in a unitary oral pharmaceutical form in the form of a thin film comprising from 0.1 mg to 100 mg of the active ingredient.

5. The process as claimed in claim 1, wherein another active ingredient or non-nano-milled particles of the active ingredient is added to the nanosuspension obtained after the mixing of at least one film-forming polymer and before the composition is converted into a thin film.

6. The process as claimed in claim 1, wherein
   a wetting agent is added to the suspension of active ingredient before said suspension is milled,
   the nanosuspension obtained after the mixing of at least one film-forming polymer is casted onto a substrate so as to obtain a film,
   the obtained film is dried.

7. The process as claimed in claim 1 wherein said solvent is water.

8. A method for the treatment of sexual dysfunction comprising the use of a composition prepared as claimed in claim 1, said composition containing up to 20 mg of tadalafil.

9. The process as claimed in claim 1, wherein the suspension obtained is milled in a wet-process ball nano-mill until 90% of the particles of the active ingredient (D(90)) have a size of less than 600 nm.

10. The process as claimed in claim 3, wherein starch derivatives are pullulans, algal derivatives are alginates, cellulose-based derivatives are ethylcellulose, hydroxypropylmethylcellulose, hydroxypropylcellulose, hydroxymethylcellulose or hydroxyethylcellulose, polyols are polyethylene glycols (PEGs).

11. The process as claimed in claim 1, wherein the prepared composition has a final water content of less than 4% (w/w).

12. The process as claimed in claim 1, wherein the suspension obtained is milled in a wet-process ball nano-mill until 90% of the particles of the active ingredient (D(90)) have a size of less than 800 nm.

* * * * *